United States Patent [19]

Hinnenkamp

[11] 4,415,473

[45] Nov. 15, 1983

[54] WATER GAS SHIFT REACTION EMPLOYING INTERCALATED METAL CARBONYL COMPLEX CATALYST COMPOSITION

[75] Inventor: James A. Hinnenkamp, Hamilton, Ohio

[73] Assignee: National Distillers and Chemical Corporation, New York, N.Y.

[21] Appl. No.: 325,180

[22] Filed: Nov. 25, 1981

Related U.S. Application Data

[62] Division of Ser. No. 207,166, Nov. 17, 1980, Pat. No. 4,324,695.

[51] Int. Cl.³ ............................................... C01B 3/16
[52] U.S. Cl. .................................................... 252/373
[58] Field of Search ................. 252/373; 423/655, 656

[56] References Cited

U.S. PATENT DOCUMENTS

| | | | |
|---|---|---|---|
| 3,539,298 | 11/1970 | Fenton | 252/373 |
| 3,847,963 | 11/1974 | Lalancette | 518/715 |
| 4,223,001 | 9/1980 | Novotny et al. | 423/655 |
| 4,226,845 | 10/1980 | Laine | 423/655 |

FOREIGN PATENT DOCUMENTS 604376  7/1948  United Kingdom ................ 423/656

OTHER PUBLICATIONS

Canadian Patent Record II 318433, Dec. 29, 1931.
Pettit et al, Inorganic Compounds with Unusual Properties II, 1979 pp. 121-130 (Advances in Chemistry Series 173).
Laine et al, J.A.C.S., 99, pp. 252-253 1977.

Primary Examiner—Howard T. Mars
Attorney, Agent, or Firm—Kenneth D. Tremain

[57] ABSTRACT

Transition metal carbonyl clusters intercalated with lamellar material such as graphite or smectites are prepared by reacting an intercalate of a transition metal halide with carbon monoxide at elevated temperature and at ambient to superatmospheric pressure. The intercalated complexes are useful in the catalysis of a variety of organic reactions including the water gas shift reaction, hydrogenation, hydroformylation, methanation, and so forth.

5 Claims, No Drawings

WATER GAS SHIFT REACTION EMPLOYING INTERCALATED METAL CARBONYL COMPLEX CATALYST COMPOSITION

This is a division of U.S. application Ser. No. 207,166 filed Nov. 7, 1980, and issued as U.S. Pat. No. 4,324,695 on Apr. 13, 1982.

BACKGROUND OF THE INVENTION

1. Field of the Invention

This invention relates to transition metal carbonyl complexes intercalated with lamellar materials. The intercalated complexes are useful as catalysts for a variety of vapor and liquid phase organic reactions, e.g., the water gas shift reaction, hydrogenation, hydroformylation, methanation, and so forth.

2. Description of the Prior Art

A number of catalytically active compositions based on graphite intercalated metal and metal compounds are known. U.S. Pat. No. 3,785,999 to Derleth et al. describes graphite-metal chloride intercation compounds, said to be useful as catalysts for the so-called Deacon process, made by contacting a mixture of graphite powder and at least one water of hydration-containing metal chloride with a stream of chlorine at elevated temperature and ambient or superatmospheric pressure. U.S. Pat. No. 3,835,067 to Schneider and U.S. Pat. No. 3,840,566 to Lalancette each describes graphite intercalated with chromium trioxide. The resulting products are intended for use in the selective oxidation of primary alcohols to aldehydes. U.S. Pat. No. 3,842,121 to Ichikawa et al. describes a catalyst capable of converting carbon monoxide into hydrocarbons which is a complex compound containing at least one alkali metal, at least one transition metal halide and graphite. Studies reported by E. Kikuchi et al., J. of Cat. 57: 27–34 (1979) and Mashinskii et al., Izv. Akad. Nauk. SSSR Khim 9, 2018 (1976) strongly suggest that the alkali metal component of the Ichikawa et al. intercalates reduces the transition metal halide component to the metallic state. U.S. Pat. No. 3,847,963 to Lalancette discloses the reaction of hydrogen and a carbon oxide to provide methane employing as catalyst, a transition metal of zero valence intercalated in graphite. U.S. Pat. No. 3,880,944 to Lalancette describes a Friedel-Crafts mixed hydrocarbon synthesis using graphite intercalated with a Lewis acid such as aluminum trichloride, aluminum tribromide and ferric bromide. The process for preparing organic fluorides described in U.S. Pat. No. 3,950,262 to Lalancette employs graphite intercalated with up to 75% by weight of antimony pentafluoride. U.S. Pat. No. 3,962,133 to Rodewald describes a process for intercalating graphite with a Lewis acid fluoride in the presence of gaseous fluorine. The resulting compositions are said to be useful catalysts for such conversion processes as cracking, isomerization, alkylation polymerization, disproportionation, dealkylation, and transalkylation. These same conversion processes are described in U.S. Pat. No. 3,984,352 to Rodewald as catalyzed with graphite having intercalated in the lattice thereof between about 5 and about 75 weight percent of a Lewis acid and optionally, a minor proportion of a Brönsted acid and/or a Group VI-B or Group VIII metal. U.S. Pat. No. 4,107,076 to Eisenberg et al. describes a catalyst system for the water gas shift reaction based on $[Rh(CO)_2Cl]_2$, aqueous HI and glacial acetic acid.

SUMMARY OF THE INVENTION

In accordance with the present invention, a transition metal carbonyl cluster intercalated with a lamellar material can be prepared by reacting an intercalate of the lamellar material and transition metal halide with carbon monoxide. The resulting composition is useful for catalyzing a number of vapor and liquid phase organic reactions including the water gas shift reaction, hydrogenation, hydroformylation, methanation, oxidation, disproportionation, and the like.

DESCRIPTION OF THE PREFERRED EMBODIMENTS

The lamellar materials which are useful in the preparation of the intercalated complexes of this invention can be selected from any of numerous compositions possessing a lamellar structure. Examples of such materials include graphite, vermiculite, smectites such as montmorillonite and hectorite, hydrated crystalline zirconium dihydrogen phosphate, and the like. Precursor graphite-transition metal halide intercalation compounds which can be employed in the manufacture of the catalysts herein are themselves known and in some cases, commercially available, e.g., Graphimet $RhCl_3$ (Ventron Corporation, Beverly, Mass.). The precursor compounds can be made to contain from about 0.5% up to about 75% by weight of transition metal halide and are readily and conveniently prepared by contacting a mixture of lamellar material with anhydrous transition metal halide, i.e., the halide and preferably the chloride, of a metal selected from Groups IVB, VB, VIB, VIIB, and VIII of the Periodic Table, in a substantially water free atmosphere and in the presence of gaseous halogen at elevated temperature, e.g., from about 200° C. up to the decomposition temperature of the resulting intercalation compound. Another useful preparative technique calls for treating mixtures of lamellar material in particulate form and transition metal powder with gaseous halogen substantially in the absence of air and water at a temperature above about 200° C. and thereafter removing contaminations which are not desired in the intercalation compounds in a purification zone at a somewhat higher temperature. In yet another method for preparing these compounds, powdered lamellar material is contacted with a water of hydration-containing metal chloride and a stream of chlorine at a temperature between 200° C. and the decomposition temperature of the intercalation compound and at a pressure between atmospheric and 5 atmospheres. Some chlorides, mainly of transition elements, can be intercalated in graphite from a solution of carbon tetrachloride at reflux temperature, in the presence of chlorine as described by Lalancette et al., Can. J. Chem., Vol 54, 2505 (1976).

Representative of transition metal halides which can be used in preparing the precursor lamellar material intercalated transition metal halides herein are such compounds as vanadium fluoride, vanadium chloride, niobium fluoride, tantalum fluoride, manganese chloride, ferric chloride, cobalt chloride, nickel chloride, osmium chloride, tungsten chloride, molybdenum chloride, rhodium chloride, iridium chloride, ruthenium chloride, platinum chloride and palladium chloride. Of the foregoing, rhodium chloride is especially preferred.

The conditions for reacting the starting lamellar material intercalated transition metal halides with carbon monoxide to convert the transition metal halides to the corresponding transition metal carbonyl clusters are not critical and can vary over a wide range of temperature and pressure. Thus, for example, a graphite intercalated transition metal halide can be reacted with carbon monoxide at temperatures of from about 30° C. to about 200° C., and preferably from about 50° C. to about 100° C., and pressures ranging from ambient to as high as 1,000 psig and even higher. The weight amount of carbon monoxide chemically incorporated into the structure of the resulting compounds can also vary over wide limits, advantageously ranging from about 1 to about 80, and preferably from about 20 to about 70, weight percent of the metal carbonyl.

The lamellar material intercalated transition metal carbonyl compositions of the present invention have unique chemical and physical properties. A wide variety of known reactions can be catalyzed by these compositions, and unexpected catalytic properties are frequently observed, e.g., in the water-gas shift reaction, when compared to a corresponding homogeneous transition metal carbonyl system, the intercalated cluster does not require added base, thus avoiding the replacement of base which has reacted with $CO_2$. Furthermore, base-resistant reactor materials are unnecessary.

Another advantage of the lamellar material intercalated transition metal carbonyl compositions of the present invention is their ease of separation from reaction products. Simple filtration or sedimentation techniques can be employed, whereas with their homogeneous counterparts, more complex techniques are required to avoid decomposition of the metal carbonyl during separation of the catalyst from reaction products.

EXAMPLE 1

This example illustrates the preparation of graphite intercalated hexadecacarbonylhexarhodium.

7.44 g of graphite intercalated with 1.5% by weight of rhodium chloride (Graphimet, manufactured by Ventron Corporation, Beverly, Mass.), and 40 ml of aqueous 90% methanol were placed in a glass liner and charged to a 300 ml autoclave reactor. Following pressurization to 400 psig with carbon monoxide and heating to 60° C., the carbon monoxide pressure within the reactor was increased to 600 psig. The contents of the reactor were stirred with pressure being periodically readjusted to maintain a level of about 600 psig. After 72 hours, the contents of the reactor were cooled to 30° C., the carbon monoxide pressure was vented, and the graphite material present in the reaction medium allowed to settle. The bulk of the methanol solution was removed by decantation with residual methanol being removed by vacuum drying at 40° C. for 2 hours. The recovered graphite intercalate was subjected to X-ray diffraction analysis which confirmed reaction of the starting graphite intercalate of rhodium chloride with carbon monoxide. Infra red spectrophotometric analysis indicated the presence of a rhodium carbonyl cluster of the formula $Rh_6(CO)_{16}$ interdispersed between graphite layers. Table I below sets forth the X-ray diffraction data for graphite, rhodium chloride-graphite intercalate and rhodium carbonyl-graphite intercalate of the present invention.

TABLE I

X-RAY DIFFRACTION DATA

| Graphite Powder (Fisher Grade #38) | | $RhCl_3$/Graphite (Alfa Graphimet) | | $Rh_6(CO)_{16}$/Graphite (New Composition) | |
|---|---|---|---|---|---|
| d(Å) | I | d(Å) | I | d(Å) | I |
| — | — | — | — | 8.11 | 5 |
| — | — | — | — | 7.43 | 4 |
| — | — | — | — | 7.37 | 4 |
| 6.65 | 3 | 6.65 | 2 | 6.65 | 4 |
| — | — | 5.90 | 3 | — | — |
| 3.35 | 430 | 3.36 | 610 | 3.36 | 460 |
| — | — | — | — | 2.96 | 1 |
| — | — | — | — | 2.77 | 2 |
| — | — | — | — | 2.34 | 2 |
| 2.13 | 13 | 2.13 | 10 | 2.13 | 11 |
| — | — | 2.08 | 14 | 2.08 | 13 |
| 2.03 | 19 | 2.03 | 30 | 2.03 | 29 |
| — | — | 1.97 | 5 | 1.97 | 5 |
| — | — | 1.80 | 4 | 1.80 | 4 |
| 1.68 | 44 | 1.68 | 32 | 1.68 | 36 |
| — | — | 1.63 | 2 | 1.63 | 2 |
| 1.55 | 3 | 1.55 | 8 | 1.54 | 13 |
| — | — | 1.47 | 1 | 1.47 | 1 |
| 1.30 | 23 | 1.31 | 12 | 1.30 | 18 |
| 1.23 | 16 | 1.23 | 19 | 1.23 | 17 |

EXAMPLE 2

This example illustrates the preparation of montmorillonite intercalated ruthenium carbonyl.

1 gm hexaamine ruthenium III chloride, $[Ru(NH_3)_6]Cl_3$ was dissolved in 50 ml deionized water under reflux accompanied by stirring. After the ruthenium complex had completely dissolved, 15 g of sodium montmorillonite was added to the solution with stirring while under reflux. An additional 25 ml of deionized water was added to the solution and the solution was refluxed overnight. The solution was filtered and the filtered material dried under a 0.3 mmHg vacuum at 65° C. for four hours. The resulting montmorillonite ruthenium complex weighed 16.67 g.

2.5 g of the montmorillonite ruthenium complex dissolved in a 10% by weight aqueous methanol solution were placed in a glass liner which was then inserted in a 70 ml Parr reactor. After flushing with carbon monoxide, the reactor was pressurized to 1000 psig with carbon monoxide at ambient temperature. Following reaction under agitation for 16 hours at 100° C., the reactor was cooled and vented, the liner was removed under a blanket of nitrogen, stoppered and a tan solid was recovered from the orange-colored methanol-containing medium by centrifuging and decanting. The tan solid was washed with about 20 ml deaerated absolute methanol and recentrifuged. The tan solid was then dried at ambient temperature under a 0.2 mmHg vacuum for 4 hours. The resulting complex was subsequently identified by infra-red analysis as sodium montmorillonite intercalated ruthenium carbonyl complex, of the formula $Ru_3(CO)_{12}$. Table II sets forth the X-ray diffraction data for montmorillonite, ruthenium exchanged montmorillonite, and $Ru_3(CO)_{12}$—montmorillonite.

TABLE II

X-RAY DIFFRACTION DATA

| "d spacing" | $Ru_3(CO)_{12}$/ montmorillonite $I/I_o$ | $RU(NH_3)_6^{3+}$/ montmorillonite $I/I_o$ | montmorillonite $I/I_o$* |
|---|---|---|---|
| 35.3 | 11 | 12 | 12 |
| 14.5 | — | 90 | — |
| 12.3 | 89 | — | 47 |
| 7.19 | 9 | — | — |
| 5.98 | 6 | — | — |

TABLE II-continued

| "d spacing" | X-RAY DIFFRACTION DATA | | |
|---|---|---|---|
| | Ru₃(CO)₁₂/ montmorillonite $I/I_o$ | RU(NH₃)₆³⁺/ montmorillonite $I/I_o$ | montmorillonite $I/I_o$* |
| 5.53 | 8 | — | — |
| 5.15 | — | 6 | — |
| 4.50 | 100 | 84 | 100 |
| 4.29 | — | — | 18 |
| 4.27 | 14 | 17 | — |
| 4.19 | 26 | — | — |
| 3.81 | 6 | — | — |
| 3.80 | — | — | 6 |
| 3.78 | — | 17 | — |
| 3.46 | — | 16 | 8 |
| 3.36 | 97 | — | 100 |
| 3.35 | — | 100 | — |
| 3.28 | — | 9 | 6 |
| 3.25 | 15 | — | — |
| 3.24 | — | — | 12 |
| 3.18 | — | 9 | — |
| 3.16 | 6 | — | — |
| 3.14 | — | — | 24 |
| 3.11 | — | 6 | — |
| 3.08 | — | — | 6 |
| 3.04 | 17 | 22 | 24 |
| 3.00 | 6 | — | 18 |
| 2.99 | — | 14 | — |
| 2.84 | 5 | — | — |
| 2.77 | 7 | — | — |
| 2.75 | 7 | — | — |
| 2.57 | 46 | 43 | 47 |
| 2.49 | — | 37 | 6 |
| 2.47 | 11 | 6 | 6 |
| 2.29 | 15 | 13 | 12 |
| 2.24 | 11 | 12 | 12 |
| 2.13 | 6 | 12 | 12 |
| 2.09 | 6 | 12 | 6 |
| 1.99 | 11 | 6 | 6 |
| 1.91 | 6 | 12 | 6 |
| 1.88 | 6 | 12 | 6 |
| 1.83 | 17 | 17 | 24 |
| 1.70 | 23 | 21 | 21 |
| 1.68 | 17 | — | 18 |
| 1.67 | — | 23 | — |
| 1.57 | 8 | — | 24 |
| 1.55 | 14 | 12 | 14 |
| 1.50 | 51 | 53 | 59 |
| 1.45 | 6 | — | — |
| 1.44 | 6 | — | — |
| 1.385 | 8 | — | 14 |
| 1.377 | 11 | 17 | 19 |
| 1.295 | 17 | — | — |
| 1.292 | — | — | 21 |
| 1.293 | — | 19 | — |
| 1.248 | 11 | 17 | 18 |
| 1.201 | 6 | 6 | 6 |
| 1.185 | 6 | 6 | 6 |

*$I/I_o$ = Relative Intensity

EXAMPLE 3

This example illustrates the use of ruthenium carbonyl cluster intercalated montmorillonite for CO reduction.

1.0 g of Ru₃(CO)₁₂/montmorillonite intercalate was charged to a 310 stainless steel reactor and tested at 735 psig with 1:1 H₂:CO fed at 7 l/hr. Results at various temperatures are summarized below:

| | Temp. °C. | | |
|---|---|---|---|
| | 278 | 331 | 383 |
| % CO Conversion | 2 | 10 | 46 |
| % Selectivity* | | | |
| CH₄ | 55 | 55 | 54 |
| C₂H₆ | 18 | 12 | 13 |
| CO₂ | 27 | 24 | 33 |
| CH₃OH | 0 | 5 | 0 |

-continued

| | Temp. °C. | | |
|---|---|---|---|
| | 278 | 331 | 383 |
| CH₃CH₂OH | 0 | 4 | 0 |

*Based on carbon

EXAMPLE 4

This example illustrates the preparation of zirconium dihydrogen phosphate intercalated rhodium carbonyl.

35 ml of 49% HF was added slowly to 45 g of zirconyl chloride dissolved in 1200 ml water. To this solution 154 ml of phosphoric acid was added dropwise. The solution was heated in a water bath at 50° C. for about 24 hours while humidified air was bubbled through the liquid. After the heating period, the solid was allowed to settle and the liquid decanted. The solid was washed with deionized water and isolated by centrifuging. After drying 18 hours at 110° C., 23.6 g of crystalline zirconium phosphate was obtained.

5 g of Zr(HPO₄)₂ $L$ and 0.5 gm RhCl₃ dissolved in 25 ml deionized water were heated to 70°-80° C. overnight accompanied by stirring. Following filtration of the reaction medium, a solid was recovered which was washed well with deionized water and dried under a vacuum of 0.3 mmHg at 80° C. for 3.5 hours. 4.7 g of RhCl₃ intercalated with Zr(HPO₄)₂ was recovered.

2.5 g of the recovered intercalate and 20 ml of a 10% aqueous methanol solution were placed in a glass liner which was then inserted into a 70 ml Parr reactor. After flushing with carbon monoxide, the reactor was pressurized to 1000 psig with carbon monoxide at ambient temperature. Following reaction under agitation for 16 hours at 100° C., the reactor was cooled and vented, the liner was removed under a nitrogen blanket, stoppered and a white-to-gray solid was recovered from the amber-colored medium by centrifuging and decanting. Following the same washing and drying procedure as in Example 2, a solid was recovered which was indicated by infra-red analysis to contain zirconium dihydrogen-phosphate intercalated rhodium carbonyl of the formula Rh₆(CO)₁₆. Table III sets forth the X-ray diffraction data for zirconium phosphate, rhodium chloride-zirconium phosphate, and rhodium carbonyl cluster-zirconium phosphate.

TABLE III

| "d spacing" | X-RAY DIFFRACTION DATA | | |
|---|---|---|---|
| | Rh₆(CO)₁₆/ Zirconium Phosphate $I/I_o$ | RhCl₃/ Zirconium Phosphate $I/I_o$ | Zirconium Phosphate $I/I_o$ |
| 9.2 | 72 | — | — |
| 8.18 | 5 | — | — |
| 7.49 | — | 100 | 100 |
| 7.56 | 17 | — | — |
| 4.52 | 33 | 31 | 14 |
| 4.44 | — | 15 | 10 |
| 3.83 | 100 | — | — |
| 3.74 | — | — | 21 |
| 3.62 | — | 31 | — |
| 3.59 | 25 | — | — |
| 3.57 | — | — | 34 |
| 3.53 | — | — | 18 |
| 3.28 | 5 | — | — |
| 3.21 | — | — | 3 |
| 3.10 | 25 | — | — |
| 2.78 | 8 | — | — |
| 2.74 | 8 | — | 4 |
| 2.66 | — | 31 | 22 |
| 2.65 | 17 | — | 15 |

TABLE III-continued

| | X-RAY DIFFRACTION DATA | | |
|---|---|---|---|
| "d spacing" | $Rh_6(CO)_{16}$/ Zirconium Phosphate $I/I_o$ | $RhCl_3$/ Zirconium Phosphate $I/I_o$ | Zirconium Phosphate $I/I_o$ |
| 2.58 | 8 | — | 8 |
| 2.54 | 8 | — | — |
| 2.51 | — | 5 | <5 |
| 2.41 | — | — | <5 |
| 2.37 | 8 | — | — |
| 2.25 | — | 5 | <5 |
| 2.19 | 8 | — | <5 |
| 2.17 | 8 | — | <5 |
| 2.13 | 8 | 8 | 7 |
| 2.05 | — | — | 5 |
| 2.03 | — | — | 5 |
| 1.96 | 8 | — | — |
| 1.89 | 8 | — | — |
| 1.86 | — | 8 | 9 |
| 1.79 | — | — | <5 |
| 1.73 | — | 8 | 5 |
| 1.70 | 17 | — | — |
| 1.67 | — | 15 | <5 |
| 1.60 | — | — | <5 |
| 1.53 | — | 15 | 8 |

EXAMPLES 5-11

These Examples illustrate the use of graphite intercalated with $Rh_6(CO)_{16}$ as catalyst for the water gas shift reaction which is represented by the equation:

$$CO + H_2O \rightleftharpoons H_2 + CO_2$$

This reaction has been used commercially for many years to increase the $H_2:CO$ ratio obtained in "syn-gas" plants. Typically iron and related metal oxides have been used as heterogeneous catalysts at temperatures above 350° C. Since hydrogen production is thermodynamically favored at lower temperatures, the lower reaction temperatures which are possible with the use of the instant catalysts results in a significant operational and economical advantage over the earlier water gas shift processes which are operable only at much high temperatures.

The catalyst composition was employed in Examples 4-9 according to the procedure: 0.50 g $Rh_6(CO)_{16}$ graphite intercalate, 10.0 ml water and 750 psig carbon monoxide in a 70 ml 316 stainless steel reactor were shaken at 150° C. for various time periods. After cooling to ambient temperature the gaseous contents of the reactor were vented, sampled and the volume measured by a wet test meter. The liquid was about neutral according to pH paper. $H_2$, $CO_2$ and CO were analyzed by gas chromatography. The $CO_2$ and $H_2$ values differed slightly and calculations were based on the assumption that $H_2$ and $CO_2$ were co-produced equally. The conditions of the reactions and the results thereof are set forth below as follows:

| WATER GAS SHIFT REACTIONS $Rh_6(CO)_{16}$/GRAPHITE INTERCALATE | | | | | | | |
|---|---|---|---|---|---|---|---|
| Example | 5 | 6 | 7 | 8 | 9 | 10 | 11** |
| CO (psig) | 750 | 750 | 750 | 750 | 750 | 750 | 800 |
| $C_2H_4$ (psig) | 0 | 0 | 0 | 750 | 0 | 0 | 0 |
| Temp. (°C.) | 150 | 150 | 150 | 150 | 150 | 150 | 135 |
| Time (hr.) | 2 | 2 | 18 | 18 | 15 | 15 | — |
| Mole Ratio KOH/$Rh_6(CO)_{16}$ | 0 | 78 | 78 | 0 | 0 | 0 | 31 |
| Moles $H_2$/ 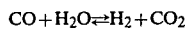 Moles $Rh_6(CO)_{16}$ (24 Hr.) | 912 | 1584 | 360 | 1560* | 392 | 332 | 115 |

*Ethylene hydroformylation products were detected. As these data show in Examples 5, 8, 9, and 10, the catalyst is active without the use of a base. Examples 6, 7 and 11** show the activities with base. Comparison of Examples 5 and 6 demonstrate the promotional effects of base. Examples 8 and 9 demonstrate the higher turnovers that are possible if the $H_2$ is removed (via ethylene hydroformylation).
**Literature data: R. M. Laine, Journal of the American Chemical Society, Vol. 100(20): 6451-6454 (1978).

EXAMPLES 12-14

These examples illustrate the use for the water gas shift reaction of various intercalated catalyst compositions according to this invention (Examples 12 and 13) compared with the use of a known non-intercalated catalyst (Example 14) the reaction conditions and results being set forth below as follows:

| Example | 12 | 13 | 14 |
|---|---|---|---|
| Intercalate | $Rh_6(CO)_{12}Zr(HPO_4)_2$ | $Ru_3(CO)_{12}$/ montmorillonite | $Ru_3(CO)_{12}$ in 86% aqueous methanol* |
| CO (psig) | 750 | 750 | 1100 |
| $C_2H_4$ (psig) | 0 | 0 | 0 |
| Temp. (°C.) | 150 | 150 | 135 |
| Time (hr.) | 2 | 2 | — |
| Mole Ratio | KOH/$Rh_6(CO)_{16}$ | KOH/$Ru_3(CO)_{12}$ | KOH/$Ru_3(CO)_{12}$ |
| | 0 | 0 | 3 |
| Moles $H_2$/ Moles $Rh_6(CO)_{16}$ | 150 | 384 | 53 |

*Literature data: Ford et al., Inorganic Compounds with Unusual Properties - II, Adv. in Chem. No. 173, P. 87 (1979).

EXAMPLE 15

This example illustrates the use of graphite intercalated $Rh_6(CO)_{16}$ as catalyst for the hydroformylation of an alkene, e.g., propylene, to aldehyde.

The hydroformylation reaction was carried out as follows: 0.50 g $Rh_6(CO)_{16}$ graphite intercalate, 10.0 ml water, 0.38 g (9.0 mM) propylene and 1500 psig $H_2/CO$ (1.5/1) in a 70 ml 316 stainless steel reactor was shaken 3 hours at 120° C. After the reaction period the reactor was cooled to ambient temperature. The gaseous products were vented, sampled, and the volume measured by wet test meter. Gas chromotographic analyses were performed on both the gas and liquid samples. The propylene conversion was nearly complete to n-butyraldehyde and isobutyraldehyde in approximately 1:1 ratio.

What is claimed is:

1. In the catalyzed water gas shift reaction, the improvement which comprises using as catalyst a catalytically effective amount of an intercalate composition comprising graphite intercalated with a transition metal carbonyl.

2. The water gas shift reaction of claim 1 wherein a base is present as a catalyst promotor.

3. In the catalyzed water gas shift reaction, the improvement which comprises using as catalyst an intercalate composition comprising a lamellar material selected from the group consisting of vermiculite, a smectite and crystalline zirconium dihydrogen phosphate intercalated with a transition metal carbonyl.

4. The reaction of claim 3 wherein the transition metal carbonyl is a transition metal carbonyl cluster.

5. The reaction of claim 3 wherein the transition metal carbonyl is a carbonyl of rhodium or ruthenium.

* * * * *